United States Patent [19]
Breslow

[11] 3,941,751
[45] Mar. 2, 1976

[54] EPOXY-AZIDO COMPOUNDS

[75] Inventor: David S. Breslow, Wilmington, Del.

[73] Assignee: Hercules Incorporated, Wilmington, Del.

[22] Filed: Mar. 6, 1974

[21] Appl. No.: 448,612

Related U.S. Application Data

[62] Division of Ser. No. 301,003, Oct. 26, 1972, abandoned, which is a division of Ser. No. 85,300, Oct. 29, 1970, abandoned, which is a division of Ser. No. 843,230, July 18, 1969, Pat. No. 3,608,604.

[52] U.S. Cl. .......... 260/75 T; 57/140 R; 57/140 C; 152/359; 260/75 S; 260/78 SC; 260/77.5 A; 260/78.4 R; 260/79.3 R; 260/80 R; 260/80 PS; 260/83.3; 260/85.5 XA; 260/85.5 S; 260/86.1 R; 260/86.7; 260/87.5 R; 260/87.7; 260/89.5 S; 260/91.1 S; 260/91.3 R; 260/92.8 A; 260/93.7; 260/214; 260/223; 260/232; 260/348 R; 260/772

[51] Int. Cl.² .......................................... C08G 63/76

[58] Field of Search ........................ 260/75 T, 96 R

[56] References Cited
UNITED STATES PATENTS
3,369,030 2/1968 MacArthur .......................... 260/349
3,814,657 6/1974 Haynes ............................ 260/75 T X

FOREIGN PATENTS OR APPLICATIONS
579,964 7/1959 Canada

*Primary Examiner*—Donald E. Czaja
*Assistant Examiner*—W. C. Danison, Jr.
*Attorney, Agent, or Firm*—Marion C. Staves

[57] ABSTRACT

Disclosed are epoxy-azido compounds of the formula

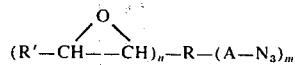

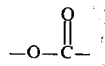

or
$-SO_2-$ where R is a polyvalent organic radical, R' is a hydrogen, alkyl, cycloalkyl, aryl, or aralkyl radical, A is and $n$ and $m$ are integers from 1 to 100. Also disclosed is the use of said epoxy-azido compounds in modifying polymers, crosslinking polymers, and adhering polymers to certain substrates, e.g. glass and other polymers.

10 Claims, No Drawings

EPOXY-AZIDO COMPOUNDS

This application is a division of my copending patent application Ser. No. 301,003, filed Oct. 26, 1972, now abandoned, which is in turn a division of application Ser. No. 85,300, filed Oct. 29, 1970, now abandoned, which is in turn a division of my application Ser. No. 843,230, filed July 18, 1969, now U.S. Pat. No. 3,608,604.

This invention relates to a new class of organic compounds and to their use. More particularly, this invention relates to a new class of epoxy-azido compounds and their use in modifying polymers, cross-linking polymers and adhering polymers to certain substrates.

The compounds of this invention are represented by the generic formula

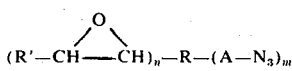

where R is a polyvalent organic radical, R' is a hydrogen, alkyl, cycloalkyl, aryl, or aralkyl radical, A is

or — $SO_2$ — and n and m are integers, broadly each being 1 to 100, most preferably from 1 to 10. Generally, R will be an organic radical selected from the group consisting of radicals derived by the removal of two or more hydrogen atoms from alkanes such as, for example, ethane, propane, butane, isobutane, pentane and its isomers, hexane and its isomers, octane and its isomers, decane and its isomers, dodecane and its isomers, octadecane and its isomers, and the like; cycloalkanes such as, for example, cyclopropane, cyclobutane, cyclopentane, cyclohexane, cyclooctane, and the like; alkylcycloalkanes, such as, for example, ethylcyclohexane, methylcyclobutane, and the like; arenes, such as, for example, benzene, naphthalene, biphenyl, and the like; alkyl substituted arene, such as, for example, toluene, ethylbenzene, o-, m- and p-xylene, o-, m- and p-diethylbenzene, and the like; alkylene-diarenes, such as, for example, diphenyl methane, 1,2-diphenylethane, 1,1-diphenylpropane, 1,3-diphenylpropane, 2,2-diphenylpropane, and the like; dialkylcycloalkanes such as, for example, 1,2-, 1,3- and 1,4-dimethylcyclohexane, 1,2- and 1,3-dimethylcyclopentane, and the like; the alkyloxyalkane, aryloxyarene, alkaryloxy arene, alkaryloxy alkarene, aralkyloxyalkane, aralkyloxyaralkane, and the like; as well as the corresponding thio and sulfonyl radicals, specific examples of which include diethyl ether, propyl butyl ether, diphenyl ether, oxy-bis(p-methyl benzene), oxy-bis(phenyl methane), diethyl thioether, diphenyl thioether, diphenylmethyl thioether, butyl sulfonyl butane, and the like radicals; and the foregoing radicals with fluoro, chloro, bromo, or iodo substituents. When an epoxyazido compound of this invention is to be used as a coupling or linking agent for polymers R preferably is substantially inert to the linking reaction.

Specific compounds of this invention represented by the foregoing generic formula include:

2,3-epoxybutyl azidoformate
9,10-epoxyoctadecyl azidoformate
4-(epoxyethyl)phenyl azidoformate
4-(epoxyethyl)phenylethyl azidoformate
3-(epoxyethyl)benzyl azidoformate
3-cyclohexyl-2,3-epoxypropyl azidoformate
4-phenyl-2,3-epoxybutyl azidoformate
4-(2,3-epoxypropyl)phenyl azidoformate
2-(2,3-epoxypropyl)phenyl azidoformate
4-(epoxyethyl)cyclohexyl azidoformate
2,3-epoxypropyl azidoformate
9,10-epoxydecyl azidoformate
9,10-epoxydecyl-2,5-diazodoformate
2,3-epoxypropyloxypropyl azidoformate
2,3-epoxypropane-1-sulfonyl azide
4-(epoxyethyl)benzenesulfonyl azide
5,6-epoxyhexane-1-sulfonyl azide
7,8-epoxyoctane-3-sulfonyl axide
11,12-epoxydodecane-3,7-disulfonyl azide
9,10-epoxyoctadecane-1-sulfonyl azide 2,3-bis(epoxyethyl)cyclohexane-2-sulfonyl azide
1-(3,4-epoxycyclohexyl)ethane-2-sulfonyl azide
4-(3,4-epoxybutyl)benzene sulfonyl azide
2-(3,4-epoxybutyl)benzene sulfonyl azide
4-(2,3-epoxypropyl)benzene sulfonyl azide
4-(2,3-epoxypropyl)benzene-1,3-disulfonyl azide
2,3-epoxypropyloxypropyl sulfonyl azide.

The epoxy-azides of this invention range from liquids to solids at room temperature and atmospheric pressure and are soluble in chlorinated hydrocarbons, aromatics, acetone, etc. They have a characteristic infrared spectrum with a strong azide peak around 2135 $cm^{-1}$. When heat is applied to the compounds of this invention they decompose giving off nitrogen; as the temperature increases the overall decomposition rate increases. The azidoformate and sulfonyl azide radicals of the compounds readily react with receptive polymers and combine therewith when heated. They also combine with ethylenically unsaturated hydrocarbon groups in a variety of compounds. In so doing, the epoxy portion of the compound remains free and unreacted. While the epoxy portion is heat stable it readily reacts when contacted with amines or carboxylic acids.

The epoxy-azido compounds of this invention can be prepared by various methods. Most preferably these compounds will be prepared by the epoxidation of an unsaturated azide compound with peracetic acid or perbenzoic acid. The reaction is usually carried out at a temperature below 100°C. in a solvent. Acetic acid is the most preferred solvent when using peracetic acid but other solvents can be used such as methylene chloride, acetone, ethyl acetate, chloroform, benzene, and the like.

As indicated above this invention includes the use of the unique epoxy-azido compounds in modifying polymers, crosslinking polymers and adhering polymers to certain substrates. All of these uses involve the reaction of the azido portion or portions of the epoxy-azido compounds with a receptive polymer. In this specification receptive polymer means a polymer having in each polymer chain at least one and generally more than one monomer unit capable of combination reaction with an azido radical of a compound of this invention, whereby the residue of the compound is chemically bonded to the polymer. Nearly all polymers are receptive polymers. Preferred examples of a receptive polymer include all types of hydrocarbon polymers including saturated and unsaturated, linear and nonlinear, crystalline and amorphous, homopolymers, copolymers, terpolymers, and the like; for example, polyethylene, polypropylene, polystyrene, styrene-butadiene rubber, butyl rubber, natural rubber, polybutadiene, polyisobutylene, ethylene--propylene copolymer, cis-1,4-polyisoprene, ethylene--propylene--dicyclopentadiene terpolymer, and the like; and blends of these polymers with each other and blends of these polymers with organic nonhydrocarbon polymers. In addition to hydrocarbon polymers preferred examples of a receptive polymer include a large number of organic nonhydrocarbon polymers including homopolymers, copolymers, terpolymers and the like. Typical of these organic nonhydrocarbon polymers are cellulose esters, such as, for example, cellulose acetate-butyrate, cellulose acetatepropionate, cellulose acetate, cellulose propionate, cellulose butyrate, and the like; cellulose ethers, such as, for example, hydroxyethyl cellulose, hydroxypropyl cellulose, and the like; polyesters such as poly(ethylene glycol terephthalate), drying and non-drying alkyd resins and the like; poly(alkylene oxide) polymers, such as poly(ethylene oxide), poly(propylene oxide), poly(ethylene oxide-propylene oxide); polyamides such as nylon, and the like; allyl pentaerythritol derivatives such as, for example, the condensate of triallyl pentaerythritol with diallylidene pentaerythritol, esters of triallyl pentaerythritol and drying oil fatty acids, and the like; poly(vinyl alkyl ethers) such as, for example, poly(vinyl methyl ether) and the like; poly(vinyl acetals) such as, for example, poly(vinyl butyral) and the like; vinyl chloride polymers having a vinyl chloride content of at least 10 mole percent, such as, for example, poly(vinyl chloride), vinyl chloride—vinyl acetate copolymers, vinyl chloride—vinylidene chloride copolymers, vinyl chloride—fumaric acid copolymers, vinyl chloride—vinyl acetal copolymers, such as, for example, the vinyl chloride—vinyl butyral copolymers, vinyl chloride—vinylidene chloride—acrylonitrile terpolymers, and the like, nitrocellulose; chlorinated natural rubber, sulfochlorinated polyethylene; polysulfide rubber; polyurethane rubber; poly(vinyl acetate); ethylene—vinyl acetate copolymers; poly (vinylidene chloride); vinylidene chloride—acrylonitrile copolymers ethyl acrylate—2-chloroethyl vinyl ether copolymers; poly (ethyl acrylate); poly(ethyl methacrylate); poly[3,3-bis(chloromethyl)oxetane]; vinyl modified poly(dimethylsiloxane); polychloroprene; butadiene—acrylonitrile copolymers; and the like.

The modified polymers of this invention resulting from the reaction of the azido portion or portions of the epoxyazido compounds with the above receptive polymers are both useful in themselves and necessary intermediates in further modifications of this invention. The amount of epoxy-azido compound used to modify a receptive polymer will depend upon the desired end use. In general, however, the amount will be from about 0.01% to about 40% by weight based on the weight of the polymer. The resulting modified polymers are quite stable and generally have physical properties similar to the unmodified polymers. However, the thus modified polymers exhibit new and improved static properties, adhesion properties, launderability, etc. Modification can be carried out by admixing the required amount of epoxy-azido compound with a receptive polymer and heating to a temperature sufficient to react the azido portion or portions of the compound with the polymer. In the case of epoxy-sulfonyl azide compounds this temperature will be in the range of from about 120°C. to about 240°C. In the case of epoxy-azidoformate compounds the temperature will be in the range of from about 80°C. to about 200°C.

In one modification of this invention the epoxy-azido compounds are used to bond various polymers to a substrate selected from siliceous materials, metals and other polymers. A typical example of the bonding process of this invention is the bonding of an α-olefin polymer such as polypropylene to a glass substrate. The said glass substrate, such as glass fibers, glass cloth, plate glass, etc., would first be treated with an amino silane compound. In so doing, the silane portion of the compound would react with the substrate, leaving the amine portion free for later reaction with an epoxy portion of an epoxy-azido compound. Next, polypropylene, having been modified with an epoxy-azido compound so as to react the azido portion with the polymer leaving the epoxy portion free, is placed in contact with the above-described treated glass. The free amine groups on the treated glass react with a free epoxy group on the modified polymer forming a tight bond between the polymer and the glass substrate.

Another typical example of bonding a polymer to a substrate using an epoxy-azido compound is the bonding of poly (ethylene terephthalate) tire cord to rubber tire stock. The polyester tire cord is first modified with the epoxy-azido compound. In so doing the azido portion or portions react with the polyester leaving the epoxy portion or portions free. Next, the tire cord is generally coated with a conventional tire cord adhesive comprising a mixture of a phenol-aldehyde resin and a rubber terpolymer latex prepared from a vinyl aryl monomer, a diene monomer, and a vinyl pyridine monomer, and then cured. If desired, the coating of conventional tire cord adhesive can be omitted with a proportionate decrease in adhesive strength. Finally, the thus treated tire cord is embedded in a vulcanizable rubber tire stock and cured. While polyester tire cords are mentioned, it will be understood that various other synthetic fibers can be incorporated in rubber tire stock in accordance with this invention. Such other tire cord fibers are for example, polyolefin, polyamide, polycarbonate, rayon, etc., and mixtures of these fibers. Improved adhesion of the synthetic fibers to the rubber tire stock can be obtained by the process of this invention no matter what the physical form of the fibers e.g. monofilament, multifilament, twisted, braided, etc. The tire cord can be treated with the epoxy-azido compound by any conventional means, for example, by dipping, spraying, brushing, or running the cord over a coated roll with a solution of the epoxy-azido compound in a suitable liquid. The epoxyazido compound can also be applied as an aqueous suspension, emulsion, or dispersion. After the epoxy-azido compound is applied, the cord is heated to a temperature at which the azido portion or portions react with the synthetic fiber. Various amounts of the epoxy-azido compound can be used. The optimum amount will depend upon the amount of modification desired, the specific epoxy-azido compound used, etc. In general, the amount added, based on the cord, will be from about 0.1% to about 10% by weight. As indicated above, the thus modified cord is generally coated with a conventional tire cord adhesive. This adhesive comprises a mixture of (1) a resin, preferably prepared from resorcinol and formaldehyde with (2) a terpolymer latex, which is preferably a styrene--butadiene--vinyl pyridine terpolymer. The vinyl pyridine content of the terpolymer is usually about 5% to about 25%, the styrene content about 5% to about 35%, and the butadiene content from about 50% to about 85%. The latex is applied to the modified tire cord by dipping, spraying, brushing, running the modified cord over a coated roll or other conventional procedure. The amount of latex added will be from about 2% to about 10% based on the weight of the cord. The thus coated cord will be cured at a temperature of from about 190°C. to about 235°C. for a period of time of from about 0.5 to about 2 minutes. The thus treated cord is then embedded in a conventional rubber tire stock and cured under pressure. The vulcanizable tire stocks in which the treated cord can be embedded as a reinforcing medium include natural rubber, and synthetic rubbers such as styrene—butadiene rubbers, ethylene—propylene—diene terpolymer rubbers, polybutadiene, polyisoprene and mixtures and blends thereof with suitable fillers, pigments, antioxidants, and cross-linking (i.e. vulcanizing) agents such as sulfur, peroxides, etc.

Another typical example of bonding a polymer to a substrate using an epoxy-azido compound is the bonding of an α-olefin polymer such as polyethylene to a metal substrate. The metal substrate will first be treated with a priming agent. The priming agent is a polyfunctional compound, such as an amino silane compound, which possesses a portion or portions which bond to the metal and another portion or portions which remain free to react with the epoxy group or groups on the epoxy-azido compounds. The process of bonding polyethylene to a metal substrate can be carried out in various ways. For example, the substrate can be coated with a solution or suspension of the priming agent, allowed to dry, then coated with a solution or suspension of the epoxy-azido compound, allowed to dry and finally contacted with the polyethylene at the decomposition temperature of the azide. By another method, the substrate can be coated with a solution or suspension of the priming agent, allowed to dry, then contacted with a solution or mixture of both the epoxy-azido compound and the polyethylene and finally heated to the decomposition temperature of the azide. By still another method the priming agent, epoxy-azido compound and polyethylene can be deposited together on the substrate and then heated.

The substrates to which the polymers may be bonded in accordance with this invention include siliceous materials such as glass, asbestos, sand, clay, concrete, stone, brick, ceramic materials, etc.; metals such as aluminum, cadmium, chromium, copper, magnesium, nickel, silver, tin, iron, titanium, zinc, etc., alloys of the metals such as steel, brass, bronze, nickel chrome, etc. and including metals which have been surface treated with phosphates, chromates, etc. or on the surface of which oxides have formed; and other polymers. By the term "other polymers" is meant any polymer other than the polymer to which it is to be bonded. These substrates to which the polymers may be bonded can be in various forms such as sheets, plates, blocks, wires, cloth, fibers, particles, etc.

In another modification of this invention the epoxyazido compounds are used to cross-link receptive polymers. The polymer to be cross-linked is admixed with from about 0.1% to about 20% by weight of an epoxy-azide compound and heated to a temperature sufficient to react the azido portion or portions of the compound with the polymer. To affect cross-linking the thus modified polymer is treated with a polyfunctional compound which will react with the free epoxy groups on the polymer. Various polyfunctional compounds can be used to affect the cross-linking, however, most preferred are the polycarboxylic acids and anhydrides such as oxalic acid, phthalic acid, phthalic anhydride, pyromellitic anhydride, etc. and the polyamines, such as m-phenylenediamine, diethylenetriamine, 4,4'-methylenedianiline, etc. When using one of these compounds, the carboxylic acid groups or amino groups react with the free epoxy groups tying together, i.e, crosslinking, the polymer chains.

The following examples will serve to illustrate the invention, all parts and percentages being by weight unless otherwise indicated.

EXAMPLE 1

This example illustrates the preparation of 2,3-epoxybutyl azidoformate.

To a slurry comprising 110 parts of sodium azide, 200 parts of water, 158 parts of acetone and 670 parts methylene chloride was added 115 parts of crotyl chloroformate with rapid stirring at room temperature. After stirring for 24 hours the orange-colored reaction mixture was diluted with 200 parts of water, separated, the organic layer washed with water, and dried over sodium sulfate. Removal of the solvent at room temperature yielded 112 parts of a clear colorless oil comprising crotyl azidoformate. A solution of 50 parts of the crotylazidoformate in 420 parts of glacial acetic acid and 3 parts of anhydrous sodium acetate was cooled to 20°C. To the crotyl azidoformate solution was added with agitation, 40% peracetic acid in an amount in excess of that required to convert the crotyl groups to epoxybutyl groups. The reaction was allowed to slowly come to room temperature and stirred until the theoretical amount of peracetic acid had been consumed. The reaction mixture was tested periodically to determine the amount of peracetic acid present. At the end of the fourth day the reaction was diluted with 600 parts of water and then extracted twice with 400 parts of methylene chloride. The methylene chloride solution was in turn washed with water and then dried over sodium sulfate. After removing the solvent 47 parts of 2,3-epoxybutyl azidoformate was obtained. The product was a light colored oil. Analysis for azide by nitrogen evolution showed that the compound contained approximately 98.7% of the theoretical amount. An analysis for oxirane oxygen showed that the compound contained approximately 91% of the theoretical amount. A typical infrared spectrum of this product displayed a strong azide peak at 2135 cm$^{-1}$.

EXAMPLE 2

This example illustrates the preparation of 9,10-epoxyoctadecyl azidoformate.

Oleyl azidoformate was prepared from oleyl chloroformate using sodium azide as described in Example 1. A solution of 84.5 parts of the oleyl azidoformate in 420 parts of glacial acetic acid containing 2 parts of sodium acetate was cooled to 20°C. To this solution was added with agitation, 40% peracetic acid in an amount in excess of that required to convert the oleyl groups to epoxyoctadecyl groups. The reaction was followed by testing for the presence of peracetic acid. After seven hours the reaction had ceased as indicated by the disappearance of peracetic acid. After 24 hours the reaction was diluted with 800 parts of methylene chloride and 600 parts of water. The methylene chloride layer was washed with water 6 times and then dried over sodium sulfate. Removal of the methylene chloride solvent left 82 parts of a colorless oil consisting essentially of 9,10-epoxyoctadecyl azidoformate. Analysis for the presence of azide by nitrogen evolution showed that the compound contained approximately 96% of the theoretical amount.

EXAMPLE 3

This example illustrates the preparation of the epoxidation product of the azidoformate of the triallyl ether of pentaerythritol.

To a solution of 43 parts of the azidoformate of the triallyl ether of pentaerythritol in 315 parts of glacial acetic acid containing 1 part of sodium acetate at room temperature was added with agitation 40% peracetic acid in an amount in excess of that required to convert one of the allyl groups to an epoxy group. After stirring for 48 hours the reaction was diluted with 750 parts of water and 535 parts of methylene chloride. The methylene chloride layer was removed and washed with water 5 times and then dried over sodium sulfate. Removal of the methylene chloride solvent left 39 parts of a clear colorless oil consisting essentially of the epoxidation product of the azidoformate of the triallyl ether of pentaerythritol. Analysis of the product indicated that it contained 13.6% azido nitrogen and 4.2% oxirane oxygen.

EXAMPLE 4

This example illustrates the preparation of 2,3-epoxy-propane-1-sulfonyl azide.

To a solution of 14.7 parts of 2-propene-1-sulfonyl azide in 105 parts of glacial acetic acid containing one part of sodium acetate was added with stirring at room temperature 40% peracetic acid in an amount in excess of that required to convert the propene radical to an epoxypropane radical. The reaction was stirred at room temperature until the peracetic acid content remained constant and then diluted with 200 parts of water and 135 parts of methylene chloride. The methylene chloride layer was removed and washed with water 5 times and then dried over magnesium sulfate. The methylene chloride solvent was removed leaving 15.1 parts of 2,3-epoxypropane-1-sulfonyl azide. The results of an infrared analysis of the product for % azido nitrogen and oxirane oxygen is tabulated below:

|  | Found | Calculated |
|---|---|---|
| % $N_3$ | 24.6 | 25.7 |
| % Oxirane oxygen | 9.3 | 9.8 |

EXAMPLE 5

This example illustrates the preparation of 4-(epoxyethyl)benzenesulfonyl azide.

To a slurry of 17.5 parts of sodium azide in 20 parts of water and 40 parts of acetone at room temperature was added with rapid stirring a solution of 18 parts of p-styrenesulfonyl chloride in 61 parts of methylene chloride. After stirring at room temperature for 18 hours the orange-colored reaction mixture was diluted with 150 parts of water and separated. The water layer was re-extracted with 61 parts of methylene chloride and then the combined methylene chloride layers were washed with water and dried over magnesium sulfate.

After removal of the methylene chloride solvent 12 parts of the resulting p-styrenesulfonyl azide was dissolved in 110 parts of glacial acetic acid containing one part of sodium acetate at 20°C. To the solution was added with agitation 40% peracetic acid in an amount in excess of that required to convert the styrene group to an epoxy ethyl benzene group. The reaction was allowed to come to room temperature and stirred until the peracetic acid content remained constant. Then it was diluted with 250 parts of water and 133 parts of methylene chloride. The methylene chloride layer was removed and washed 6 times with water and then dried over sodium sulfate. The methylene chloride solvent was removed to give 12.5 parts of 4-(epoxyethyl)benzenesulfonyl azide. The product was analyzed by infrared analysis for azide nitrogen and oxirane oxygen. The results of this analysis are tabulated below:

|  | Found | Calculated |
|---|---|---|
| % $N_3$ | 17.9 | 18.6 |
| % Oxirane oxygen | 6.5 | 7.1 |

EXAMPLE 6

This example illustrates the use of the epoxysulfonyl azide of Example 5 in cross-linking polyethylene.

A slurry of 100 parts of high density polyethylene, 0.5 part 4,4'-thio-bis(6-tertiary-butyl-m-cresol) antioxidant and 5 parts 4-(epoxyethyl)benzenesulfonyl azide in acetone was prepared. The acetone was removed at 50°C. and the polymer reacted with the epoxy-azide by heating at 170°C. for 30 minutes. Ten parts of the thus modified polyethylene was admixed with 0.15 part diethylenetriamine on a two-roll mill and then heated for 30 minutes at 160°C. A control sample of the polymer was treated exactly the same way except for the addition of the epoxy-azido compound. The two samples were tested for cross-linking by soaking in decahydronaphthalene at 140°C. The sample containing the epoxy-azide was insoluble in the decahydronaphthalene solvent, indicating cross-linking. The control sample, on the other hand, was completely soluble.

EXAMPLE 7

This example illustrates the use of epoxy-azido compound of Example 1 in bonding polypropylene to glass cloth.

Twelve ply laminates of glass cloth and polypropylene film were prepared using 181 style electrical glass woven cloth, heat cleaned and having a weight of 8.9 ounces per sq. yd., and 5 mil film of crystalline polypropylene having a melt index ($I_2$ at 230°C.) of 4.0. Sheets of the glass cloth were immersed in a benzene solution of γ-aminopropyltriethoxysilane and 2,3-epoxybutyl azidoformate. The two ingredients were present in the solution in approximately a 1:1 mole ratio. The thus treated cloth was allowed to dry overnight and then laid up to form the laminate by alternating plies of the treated glass cloth and sheets of the polypropylene film. The resulting assembly was compression molded at a temperature of 220°C. for 5 minutes at contact pressure, 3 minutes at 220°C. under a pressure of 500 p.s.i. and then cooled to 23°C. under 500 p.s.i. pressure to form a ⅛ inch thick laminate. A control laminate was prepared exactly as described above except for the omission of the epoxy-azido compound. Test specimens 1 in. × 3 in. were cut from the laminates and tested for flexural strength according to ASTM D-790 on a two-inch span at 0.05 in. per min. cross-head speed. The results are tabulated below:

|  | Flexural strength (psi) |
| --- | --- |
| Treated sample | 28,000 |
| Control | 18,000 |

EXAMPLE 8

This example illustrates the use of the epoxy-azido compound of Example 3 to improve the adhesion of polyester tire cord to rubber tire stock.

Poly(ethylene terephthalate) tire cord 1,000 denier and 3 ply under about 500 grams of tension was passed twice through a trough containing a 5% solution of the epoxy-azido compound in trichloroethylene. The cord was next passed through two ovens in series at 200°F. and 400°F. Residence times in the ovens were 65 and 54 seconds respectively. The cord dip pick-up was approximately 1% by weight. The modified cord was next coated with a conventional latex adhesive, prepared as follows: To a solution of 0.24 part of sodium hydroxide in 192.8 parts of water was added 8.8 parts of resorcinol with continued stirring until a complete solution was achieved. Then 12.2 parts of 37% formaldehyde was added. The solution was aged for approximately 5 hours at about 75°C. and then added slowly to a mixture of 48 parts water and 195 parts of a latex comprising a terpolymer of styrene, butadiene and vinyl pyridine, the monomers being present in a ratio of approximately 50:70:15. The mixture was stirred slowly for 15 minutes and its pH adjusted to 10.3 using concentrated ammonium hydroxide. The resulting gray-violet latex contained approximately 20% solids. The epoxy-azido modified cord was passed twice through a trough of the latex under a tension of 500 grams and then dried and cured for 54 seconds at a temperature of 430°F.

The thus coated cord was then vulcanized with a rubber tire stock in the form of ⅜ inch H-specimens. The rubber tire stock has the following formulation:

| Compounds | Parts |
| --- | --- |
| Natural rubber (smoked sheet) | 80 |
| Styrene butadiene rubber | 20 |
| Semi-reinforcing furnace black | 25 |
| Zinc Oxide | 5 |
| Stearic Acid | 2 |
| Polytrimethyldihydroquinoline | 1 |
| Heavy pine tar | 0.5 |
| Benzothiazyl disulfide | 1 |
| Tetramethyl thiuram disulfide | 0.1 |
| Sulfur | 2.6 |

The test specimens were cured for 45 minutes at a temperature of 307°F. After several hours conditioning at room temperature the H-specimens were pulled apart on a tester according to the procedure of ASTM D-2138-62T. An average (6 test specimens) of 35.7 pounds was required to overcome the tire cord-rubber adhesion. A control specimen treated exactly the same as above except for the epoxy azido modification of the tire cord gave an average of 12.6 pounds required to overcome the tire cordrubber adhesion.

What I claim and desire to protect by Letters Patent is:

1. A polymer selected from hydrocarbon polymers, cellulose esters, cellulose ethers, polyesters, poly(alkylene oxide) polymers, polyamides, allyl pentaerythritol derivatives, poly(vinyl alkyl ethers), poly(vinyl acetals), vinyl chloride polymers, nitrocellulose, chlorinated natural rubber, sulfochlorinated polyethylene; polysulfide rubber, polyurethane rubber, poly(vinyl acetate), ethylene—vinyl acetate copolymers, poly(vinylidene chloride), vinylidene chloride—acrylonitrile copolymers, ethyl acrylate—2-chloroethyl vinyl ether copolymers, poly(ethyl acrylate), poly(ethyl methacrylate), poly[3,3-bis(chloromethyl)oxetane], vinyl modified poly(dimethylsiloxane), polychloroprene, and butadiene--acrylonitrile copolymers, modified by reaction with an epoxy-azido compound having the formula

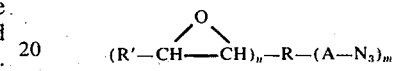

where R is an organic radical selected from the group consisting of radicals derived by the removal of two or more hydrogen atoms from alkanes, cycloalkanes, alkylcycloalkanes, arenes, alkyl substituted arenes, alkylene-diarenes, dialkylcycloalkanes, alkyloxyalkanes, aryloxyarenes, alkaryloxyarenes, alkaryloxyalkarenes, aralkyloxyalkanes, aralkyloxyaralkanes, alkylthioalkanes, arylthioarenes, alkarylthioarenes, alkarylthioalkarenes, aralkylthioalkanes, aralkylthioaralkanes, alkylsulfonylalkanes, arylsulfonylarenes, alkarylsulfonylarenes, alkarylsulfonylalkarenes, aralkylsulfonylalkanes, aralkylsulfonylaralkanes, and the foregoing radicals with fluoro, chloro, bromo or iodo substituents, R' is a radical selected from the group consisting of hydrogen, alkyl, cycloalkyl, aryl, and aralkyl radicals, A is a radical selected from the group consisting of

and —SO$_2$— and $n$ and $m$ are integers from 1 to 10.

2. A process for making a modified polymer which comprises heating a polymer selected from hydrocarbon polymers cellulose esters, cellulose ethers, polyesters, poly(alkylene oxide) polymers, polyamides, allyl pentaerythritol derivatives, poly(vinyl alkyl ethers), poly(vinyl acetals), vinyl chloride polymers, nitrocellulose, chlorinated natural rubber, sulfochlorinated polyethylene; polysulfide rubber, polyurethane rubber, poly(vinyl acetate), ethylene—vinyl acetate copolymers, poly(vinylidene chloride), vinylidene chloride—acrylonitrile copolymers, ethyl acrylate—2-chloroethyl vinyl ether copolymers, poly(ethyl acrylate), poly(ethyl methacrylate), poly[3,3-bis(chloromethyl)oxetane], vinyl modified poly(dimethylsiloxane), polychloroprene, and butadiene--acrylonitrile copolymers, in contact with a small amount of an epoxy-azido compound having the formula

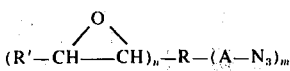

where R is an organic radical selected from the group consisting of radicals derived by the removal of two or more hydrogen atoms from alkanes, cycloalkanes, alkylcycloalkanes, arenes, alkyl substituted arenes, alkylene-diarenes, dialkylcycloalkanes, alkyloxyalkanes, aryloxyarenes, alkaryloxyarenes, alkaryloxyalkarenes, aralkyloxyalkanes, aralkyloxyaralkanes, alkylthioalkanes, arylthioarenes, alkarylthioarenes, alkarylthioalkarenes, aralkylthioalkanes, aralkylthioaralkanes, alkylsulfonylalkanes, arylsulfonylarenes, alkarylsulfonylarenes, alkarylsulfonylalkarenes, aralkylsulfonylalkanes, aralkylsulfonylaralkanes, and the foregoing radicals with fluoro, chloro, bromo or iodo substituents, R' is a radical selected from the group consisting of hydrogen, alkyl, cycloalkyl, aryl, and aralkyl radicals, A is a radical selected from the group consisting of

and —SO$_2$— and $n$ and $m$ are integers from 1 to 10.

3. The modified polymer of claim 1 wherein the polymer is a polyester.

4. The modified polymer of claim 1 wherein the polymer is a hydrocarbon polymer.

5. The modified polyester of claim 3 wherein the polymer is in the form of fibers.

6. The modified hydrocarbon polymer of claim 4 wherein the polymer is in the form of a film.

7. The modified polymer of claim 4 wherein the hydrocarbon polymer is polypropylene.

8. The modified polymer of claim 3 wherein the polyester is poly(ethylene terephthalate).

9. A polyester modified by reaction with an epoxy-azido compound having the formula

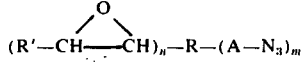

where R is an organic radical selected from the group consisting of radicals derived by the removal of two or more hydrogen atoms from alkanes, cycloalkanes, alkylcycloalkanes, arenes, alkyl substituted arenes, alkylene-diarenes, dialkylcycloalkanes, alkyloxyalkanes, aryloxyarenes, alkaryloxyarenes, alkaryloxyalkarenes, aralkyloxyalkanes, aralkyloxyaralkanes, alkylthioalkanes, arylthioarenes, alkarylthioarenes, alkarylthioalkarenes, aralkylthioalkanes, aralkylthioaralkanes, alkylsulfonylalkanes, arylsulfonylarenes, alkarylsulfonylarenes, alkarylsulfonylalkarenes, aralkylsulfonylalkanes, aralkylsulfonylaralkanes, and the foregoing radicals with fluoro, chloro, bromo or iodo substituents, R' is a radical selected from the group consisting of hydrogen, alkyl, cycloalkyl, aryl, and aralkyl radicals, A is a radical selected from the group consisting of

and —SO$_2$— and $n$ and $m$ are integers from 1 to 10.

10. A process for making a modified polyester which comprises heating said polyester in contact with a small amount of an epoxy-azido compound having the formula

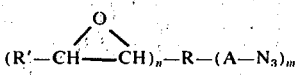

where R is an organic radical selected from the group consisting of radicals derived by the removal of two or more hydrogen atoms from alkanes, cycloalkanes, alkylcycloalkanes, arenes, alkyl substituted arenes, alkylene-diarenes, dialkylcycloalkanes, alkyloxyalkanes, aryloxyarenes, alkaryloxyarenes, alkaryloxyalkarenes, aralkyloxyalkanes, aralkyloxyaralkanes, alkylthioalkanes, arylthioarenes, alkarylthioarenes, alkarylthioalkarenes, aralkylthioalkanes, aralkylthioaralkanes, alkylsulfonylalkanes, arylsulfonylarenes, alkarylsulfonylarenes, alkarylsulfonylalkarenes, aralkylsulfonylalkanes, aralkylsulfonylaralkanes, and the foregoing radicals with fluoro, chloro, bromo or iodo substituents, R' is a radical selected from the group consisting of hydrogen, alkyl, cycloalkyl, aryl, and aralkyl radicals, A is a radical selected from the group consisting of

and —SO$_2$— and $n$ and $m$ are integers from 1 to 10.

* * * * *

UNITED STATES PATENT AND TRADEMARK OFFICE
CERTIFICATE OF CORRECTION

PATENT NO.   : 3,941,751
DATED        : March 2, 1976
INVENTOR(S)  : David S. Breslow It is certified that error appears in the above-identified patent and that said Letters Patent are hereby corrected as shown below:

In the Abstract, after the first formula the following should be inserted and the same deleted after the third formula;

"where R is a polyvalent organic radical, R' is a hydrogen, alkyl, cycloalkyl, aryl, or aralkyl radical, A is"

Signed and Sealed this

Twenty-seventh Day of July 1976

[SEAL]

Attest:

RUTH C. MASON
*Attesting Officer*

C. MARSHALL DANN
*Commissioner of Patents and Trademarks*